United States Patent [19]
Hickey

[11] 3,987,505
[45] Oct. 26, 1976

[54] RESTRAINING DEVICE

[76] Inventor: Wilma Jayne Hickey, 240 NW. 16th St., Ontario, Oreg. 97914

[22] Filed: Jan. 14, 1976

[21] Appl. No.: 648,979

Related U.S. Application Data

[63] Continuation of Ser. No. 540,069, Jan. 10, 1975, abandoned.

[52] U.S. Cl. .................................................. 5/336
[51] Int. Cl.² ............................................. A47G 9/00
[58] Field of Search .............. 5/334 A, 334 C, 335, 5/336; 2/69.5

[56] References Cited
UNITED STATES PATENTS

| | | |
|---|---|---|
| 2,325,097 | 7/1943 | Behringer............................ 5/334 C |
| 2,651,781 | 9/1953 | Buchholz.............................. 2/69.5 |
| 2,845,513 | 11/1974 | Hubner................................. 5/336 |

*Primary Examiner*—Paul R. Gilliam
*Assistant Examiner*—Andrew M. Calvert

[57] ABSTRACT

A bed-fitted patient restraining device comprises a mattress cover fabricated to conform about the top mattress of a bed; and a restraint jacket including a pair of complementary panels corresponding to front panels of a sleeveless bodice garment, the panels being secured at their upper ends and sides corresponding to sides and shoulder portions of the garment, with openings through which the patient's arms may be disposed, matable edges of the jacket panels being provided with fasteners, arm restraining straps disposed centrally at the sides of the jacket panels, and a crotch restraint.

3 Claims, 1 Drawing Figure

U.S. Patent Oct. 26, 1976 3,987,505
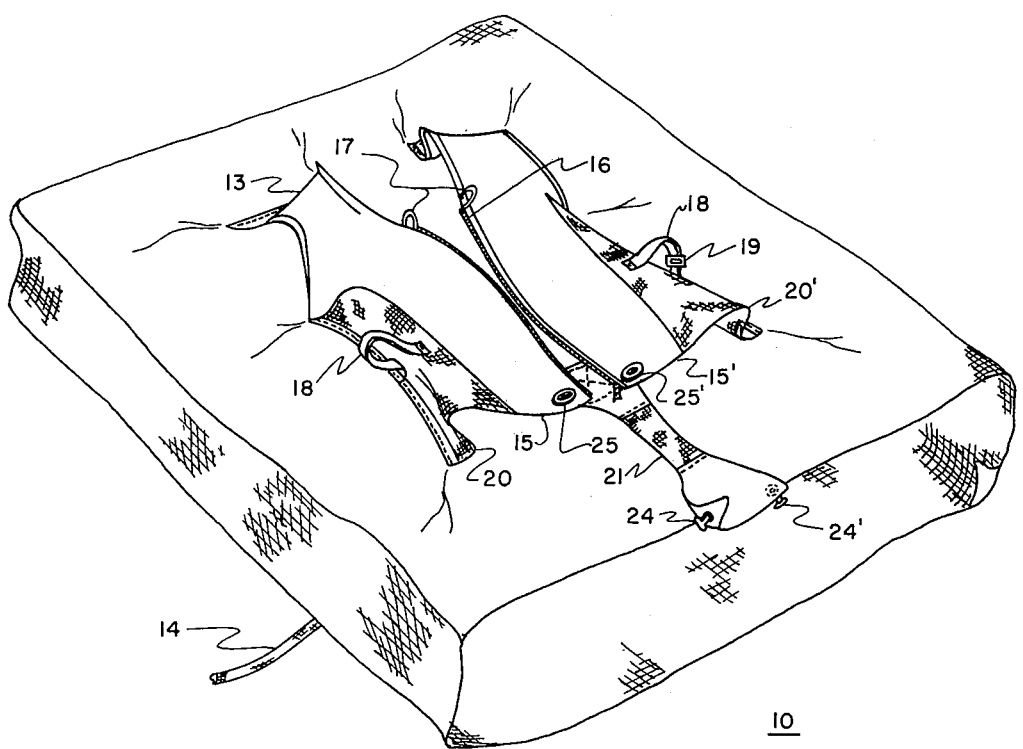

RESTRAINING DEVICE

REFERENCE TO OTHER APPLICATIONS

This application is a continuation of and claims priority on Ser. No. 540,069 filed Jan. 10, 1975, now abandoned.

FIELD OF THE INVENTION

The present invention relates to patient restraining devices and more particularly to a bed-fitted patient restraining device.

DESCRIPTION OF THE PRIOR ART

A great variety of means have been offered in the prior art to restrain patients on beds, or to restrain mobility of a patient who is on a bed. These means have included tying the patient by means of a harness to the bed frame structure, or disposing the patient in a sack-like enclosure which is then securable to the bed.

It is clear that means provided in the prior art have the serious limitation that the patient must be elevated in order to dispose harness or sack members under the patient's body. It is also clear that any means on which the patient must lie for extended periods will have the effect of injuring the patient resulting in bed sores and the like.

Accordingly, it is an object of the present invention to provide a bed-fitted patient restraining device which provides nothing injurious on which the patient is forced to lie.

It is a further object of this invention that the aforesaid restraining device be employable with bed linen to facilitate care and maintenance in large scale laundry operations.

These and other objects shall become apparent from the description following, it being understood that modifications may be made without affecting the teachings of the invention here set out.

SUMMARY OF THE INVENTION

A bed-fitted patient restraining device comprises a mattress cover fabricated to conform about the top mattress of a bed; and a restraint jacket including a pair of complementary panels corresponding to front panels of a sleeveless bodice garment, the panels being secured at their upper ends and sides corresponding to sides and shoulder portions of the garment, with openings through which the patient's arms may be disposed, matable edges of the jacket panels being provided with fasteners, arm restraining straps disposed centrally at the sides of the jacket panels, and a crotch restraint.

A more thorough and comprehensive understanding may be had from the detailed description of the preferred embodiment when read in connection with the drawings forming a part of this specification.

BRIEF DESCRIPTION OF DRAWINGS

FIG. 1 is a perspective view of the bed-fitted patient restraining device of this invention as it would appear installed on a mattress.

DETAILED DESCRIPTION OF THE PREFERRED EMBODIMENT

Referring now to the FIG. 1, the bed-fitted patient restraining device of this invention is shown to advantage and generally identified by the numeral 10. The device 10 is intended to be mounted on a commonly known mattress or the like. The device 10 comprises a fitted mattress cover 11, cover retaining straps 14, and a restraint jacket 13. The mattress cover 11 may be fabricated in the manner of mattress covers of the prior art.

It should be pointed out that the material from which the mattress cover 11 is fabricated should be sufficiently heavy to withstand high force which the patient may apply. The lower perimeter edge of the mattress cover 11 is provided with straps 14 which are disposed under the mattress (not shown) and secured to complementary means provided in the opposite side of the cover 11.

The jacket 13 comprises a pair of panels 15 and 15' which are substantially similar to left and right front panels of a sleeveless jacket, shirt or bodice found in garments. Perimeter edges corresponding to the sides and shoulders of the panels 15 and 15' are bound to the top portion of the mattress cover 11. This configuration leaves holes through which the patient's arms may be disposed, a void between the top of the panels 15 and 15' corresponding to the neck, and free lower edges of the panels 15 and 15' which cover the abdominal region of the patient are secured by a jacket fastener which may be a zipper 16, buttons, VELCRO strips or the like. Additional securing eyelets 17 may be disposed at the upper and lower ends of the zipper 16, and be secured by clips (not shown), laces or the like. Arm restraining straps 18 are disposed centrally at each side of the panels 15 and 15'. The straps 18 may be adjustable or resilient to secure various sizes of arms. The straps 18 may be provided with adjusting buckles 19. The panels 15 and 15' may be provided with means making it possible to secure various sizes of patients by providing resilient side members 20 and 20' in the panels 15 and 15' respectively. The members 20 and 20' may be fabricated of rubber, elastic or similar materials.

A crotch support 21 may be provided to prevent the patient from sliding out of the bottom of the jacket 13. The crotch restraint 23 may be a resilient member bound to the top of the mattress cover 11 centrally between the lower terminal ends of the panels 15 and 15'. The free end of the restraint 23 is provided with a pair of clip fasteners 24 and 24' which engage eyelets 25 and 25' in the panels 15 and 15' respectively.

I claim:

1. A bed-fitted patient restraining device, comprising:
    a mattress cover being fabricated to conform about the top mattress of a bed, said mattress cover including means for securing said mattress cover to said mattress; and
    a restraint jacket including a pair of complementary panels corresponding to front panels of a sleeveless bodice garment, said panels being secured at their upper ends and sides corresponding to sides and shoulder portions of said garment, with openings through which the patient's arms may be disposed, matable edges of said jacket panels being provided with fasteners, arm restraining straps disposed centrally at the sides of said jacket panels, and a crotch restraint being a strap bound to said mattress cover centrally between the lowermost terminal ends of said panels, the free end of said crotch restraint being provided with detachable fasteners which may engage complementary fastener portions at the lower interior ends of said panels.

2. The article of claim 1 wherein said jacket panels are provided with resilient elastomeric members permitting various sizes of patients to be accommodated.

3. The article of claim 1 wherein said arm straps are provided with means adjustable to various sizes of patients.

* * * * *